United States Patent [19]

Veber

[11] 4,146,612
[45] Mar. 27, 1979

[54] SOMATOSTATIN ANALOGS

[75] Inventor: Daniel F. Veber, Ambler, Pa.

[73] Assignee: Merck & Co., Inc., Rahway, N.J.

[21] Appl. No.: 920,529

[22] Filed: Jun. 29, 1978

Related U.S. Application Data

[63] Continuation-in-part of Ser. No. 804,678, Jun. 8, 1977, abandoned.

[51] Int. Cl.² .................... A61K 37/00; C07C 103/52
[52] U.S. Cl. ............................... 424/177; 260/112.5 S
[58] Field of Search ................. 260/112.5 S; 424/177

[56] References Cited

U.S. PATENT DOCUMENTS

| | | | |
|---|---|---|---|
| 781,610 | 3/1977 | Veber et al. | 260/112.5 S |
| 3,882,098 | 5/1975 | Sarantakis | 260/112.5 S |
| 3,904,594 | 9/1975 | Guillemin | 260/112.5 S |
| 3,933,784 | 1/1976 | Sarantakis | 260/112.5 S |
| 4,011,182 | 3/1977 | Sarantakis | 260/112.5 S |

FOREIGN PATENT DOCUMENTS 2460469  7/1976  Fed. Rep. of Germany .... 260/112.5 S

OTHER PUBLICATIONS

Rivier, et al., J. Med. Chem. 19, 1010 (1976).
Rivier, et al., J. Med. Chem. 18, 123 (1975).
Brown, et al., Endocrinology 98, 336 (1976).
Brown, et al., Biochem. Biophysical Res. Commun. 65, 746 (1975).
Ependic, et al., Febs. Letters 58(1), 302-305 (1975).
Veber, et al. J.A.C.S. 98, 2367 (1976).

*Primary Examiner*—Delbert R. Phillips
*Attorney, Agent, or Firm*—Walter Patton; Harry E. Westlake, Jr.

[57] ABSTRACT

Somatostatin analogs having the structural formula:

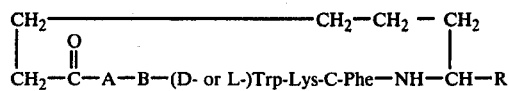

wherein
A is Phe, Tyr, O-Me-Tyr,
B is Phe, Tyr,
C is Thr, Val,
R is H or COOH, wherein the ring formed by the peptide backbone contains 26 atoms and pharmaceutically acceptable non-toxic acid addition salts and carboxylic acid salts thereof are prepared by the solid phase method. These peptides have the property of inhibiting release of insulin, inhibiting growth hormone release and inhibiting glucagon release in humans and animals without materially affecting gastric secretion.

3 Claims, No Drawings

SOMATOSTATIN ANALOGS

CROSS REFERENCE TO RELATED APPLICATIONS

This is a continuation-in-part application of co-pending application Ser. No. 804,678, filed June 8, 1977, now abandoned.

BACKGROUND OF THE INVENTION:

Somatostatin is a tetradecapeptide having the structure:

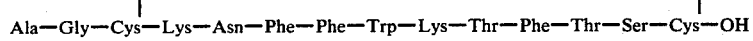

and has the properties of inhibiting the release of growth hormone, inhibiting the release of insulin and glucagon and reducing gastric secretion. This lack of specificity of the biological activity of somatostatin has led to an intensive search for analogs which exhibit a more specific biological activity. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself. The present invention provides somatostatin analogs having no material affect on gastric secretion and a longer duration of action and a novel method for preparing said analogs.

The present invention further provides somatostatin analogs which are easier to prepare because they contain only 26 atoms in the peptide backbone.

SUMMARY OF THE INVENTION

This invention is concerned with novel somatostatin analogs having a more specific biological activity and duration of activity than naturally occurring somatostatin and which are easier to prepare because of the smaller ring size and having the structural formula:

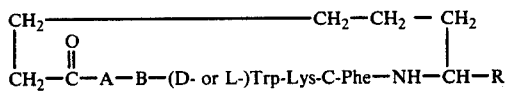

wherein
A is Phe, Tyr, O-Me-Tyr,
B is Phe, Tyr,
C is Thr, Val,
R is H or COOH
wherein the ring formed by the peptide backbone contains 26 atoms and pharmaceutically acceptable non-toxic acid addition salts and carboxylic acid salts thereof.

The preferred somatostatin analogs of the present invention are illustrated by the following structural formula:

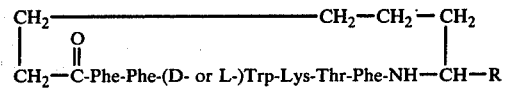

wherein R is H or COOH,
and the pharmaceutically acceptable non-toxic acid addition salts and carboxylic acid salts thereof.

Illustrative of acid addition salts are hydrochloride, hydrobromide, sulfate, phosphate, maleate, acetate, citrate, benzoate, succinate, malate, ascorbate and the like. The acid addition salts can be conveniently prepared by dissolving the above novel compounds in water, adding two equivalents of appropriate acid and lyophilizing.

The products of this invention having a carboxylic acid group form a wide variety of pharmaceutically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Illustrative examples include salts derived from sodium hydroxide, sodium carbonate, sodium bicarbonate, potassium carbonate, potassium hydroxide, calcium carbonate, trimethylamine, triethylamine piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts can be mono-salts such as the mono-sodium salt obtained by treating one equivalent of sodium hydroxide with one equivalent of the product, or they may also be mixed di-salts. Such salts may be obtained by treating one equivalent of a base having a divalent cation, such as calcium hydroxide, with one equivalent of the product. The salts of this invention are pharmacologically acceptable non-toxic derivatives which can be used as the active ingredient in suitable unit-dosage pharmaceutical forms.

The somatostatin analogs of the present invention differ from somatostatin by virtue of the fact that they lack an N-terminal amino group thus eliminating the group involved in enzymic cleavage of the molecule by aminopeptidases. Furthermore, the deletion of the adjacent heteroatoms of the disulfide bridge of somatostatin increases the stability of the analogs in vivo by preventing enzymatic degradation by reductive cleavage. Therefore, the analogs of the present invention are more resistent to cleavage in vivo than somatostatin and thus have a prolonged duration of action.

Somatostatin is a tetradecapeptide having the structure:

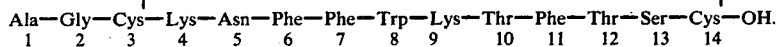

Ala—Gly—Cys—Lys—Asn—Phe—Phe—Trp—Lys—Thr—Phe—Thr—Ser—Cys—OH.
 1    2    3    4    5    6    7    8    9    10   11   12   13   14

The portion of somatostatin extending from amino acid Cys[3] to Cys[14] forms a dodecapeptide of the following structure:

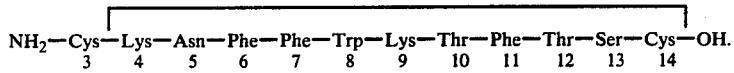

NH$_2$—Cys—Lys—Asn—Phe—Phe—Trp—Lys—Thr—Phe—Thr—Ser—Cys—OH.
       3    4    5    6    7    8    9    10   11   12   13   14

The peptide backbone and the disulfide bridge consist of a continuous 38 atom ring.

The present invention provides somatostatin analogs wherein the Ala[1]-Gly[2], Lys[4]-Asn[5], Thr[12]-Ser[13] and the amino group of Cys[3] are deleted. Furthermore, the disulfide atoms of the cystine, —S—S—, have been replaced by the dicarba group, —CH$_2$—CH$_2$. Whereas, in somatostatin the amino acids 4 and 13 are bridged by cystine, the present invention provides somatostatin analogs wherein amino acids 6 and 11 are bridged by 7-aminoheptanoic acid or (D- or L-)α-aminosuberic acid. The resulting ring contains 26 atoms. Furthermore, the somatostatin analogs of the present invention include those wherein Phe[6] is replaced by Tyr or O-Me-Tyr; Phe[7] is replaced by Tyr; Trp[8] is replaced by D-Trp and Thr[10] is replaced by Val.

The abbreviated designations, which are used herein for the amino acid components, certain preferred protecting groups, amino acid activating groups, condensing agents, reagents and solvents employed in the process of this invention are as follows:

TABLE I

| Abbreviated Designation | Amino acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| O-Me-Tyr | L-O-Me-tyrosine |
| Val | L-valine |
| Asu | (D- or L-)α-aminosuberic acid |

| Abbreviated Designation | Protecting Groups |
|---|---|
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |

| Abbreviated Designation | Activating Groups |
|---|---|
| ONp | p-nitrophenyl ester |
| HSE | N-hydroxysuccinimide ester |
| HBT | 1-hydroxybenzotriazole |

| Abbreviated Designation | Condensing Agents |
|---|---|
| DCCI | dicyclohexylcarbodiimide |

TABLE I-continued

| Designation | Reagents |
|---|---|
| TFA | trifluoroacetic acid |
| TEA | triethylamine |
| DIPEA | diisopropylethylamine |

| Abbreviated Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel somatostatin analogs are prepared by cyclizing corresponding linear peptides. The linear peptides are prepared by using the solid phase sequencial synthesis technique. Accordingly, the process for preparing the somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic peptide; and (e) removing the remaining blocking groups.

When the linear peptide is prepared on the resin, it is not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. As an example to illustrate this, either of the two following linear peptides, when cyclized, will give the identical somatostatin analog:

D—Trp-(ε-2-Cl—CBZ)Lys—(O—Bzl)Thr—Phe—Aha—Phe—Phe—N$_3$
or
Aha—Phe—Phe—D—Trp-(ε-2-Cl—CBZ)Lys—(O—Bzl)Thr—Phe—N$_3$

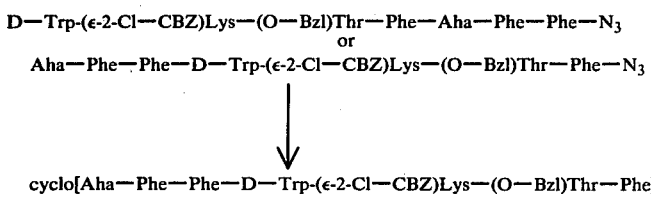

cyclo[Aha—Phe—Phe—D—Trp-(ε-2-Cl—CBZ)Lys—(O—Bzl)Thr—Phe].

It is evident that since the linear peptide is going to be cyclized, it does not matter which amino acid is used to start the chain. Starting with Phe at the carboxyl end, as illustrated in the first of the two examples above, has an advantage over the second example. In the first example, D-Trp, which reacts with t-butyl carbonium ions formed when BOC groups are removed, is the N-terminal amino acid and thus will be added last and hence will be subjected to the least number of exposures to t-butyl carbonium ion.

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or hydrogen chloride in ethyl acetate).

The —OH group of Thr can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about $-40°$ C. and $+20°$ C. Alternatively, the peptide may be removed from the resin by treatment with a lower alcohol such as methanol in the presence of an organic base such as triethylamine, thus resulting in the formation of the corresponding lower alcohol ester of the linear hexapeptide. In the case wherein the ester is the methyl ester, the resulting compound may be converted to the azide via the hydrazide which may then be cyclized to the desired cyclic peptide. The preferred method in the present invention is the use of hydrazine.

Table II

General Scheme for Preparing Cyclo (Aha—Phe—Phe—D—Trp—Lys—Thr—Phe)

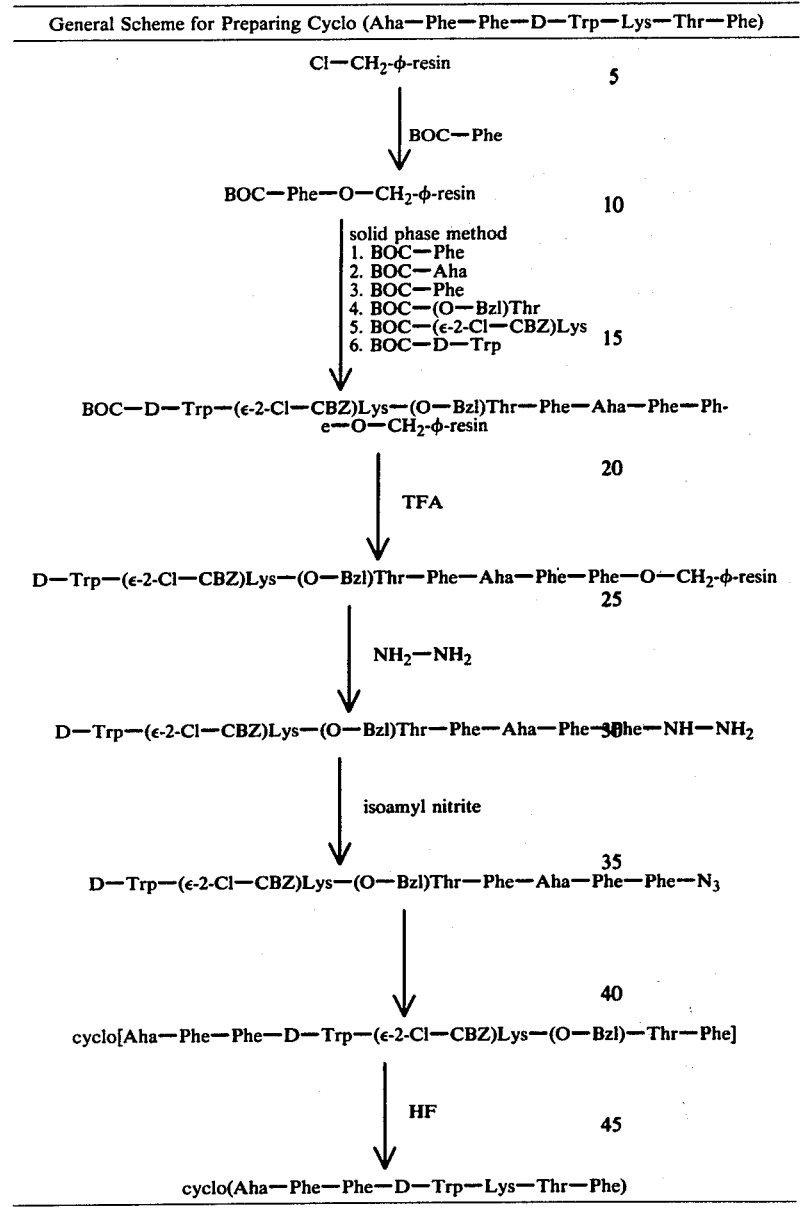

As reference to Table II will show, one preferred overall procedure for preparing the desired cyclic peptides of the present invention involves the stepwise synthesis of the linear peptide on a solid phase resin. More specifically, in the process for preparing cyclo(Aha-Phe-Phe-D-Trp-Lys-Thr-Phe), the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence: D-Trp-($\epsilon$-2-Cl-CBZ)Lys-(O-Bzl)Thr-Phe-Aha-Phe-Phe-NH-$NH_2$ is treated with isoamyl nitrite in acid pH to form the corresponding azide. The azide solution is diluted with solvent and neutralized with an organic base. The linear peptide cyclizes to form cyclo[Aha-Phe-Phe-D-Trp-($\epsilon$-2-Cl-CBZ)Lys-(O-Bzl)Thr-Phe].

During the cyclization the "pH" is checked and maintained at neutral by the addition of organic base. The "pH" in organic solvent is determined by the application of an aliquot of the solution to narrow range pH paper.

After the linear peptide is cyclized, the remaining protective groups, 2-Cl-CBZ and Bzl, are removed in one step by treatment with HF in the presence of anisole. The crude cyclic peptides obtained by the processes of Table II are purified by chromatography, preferably on Sephadex eluted with 50% aqueous acetic acid.

TABLE III

General Scheme for Preparing Cyclo(D—Asu—Phe—Phe—D—Trp—Lys—Thr—Phe)

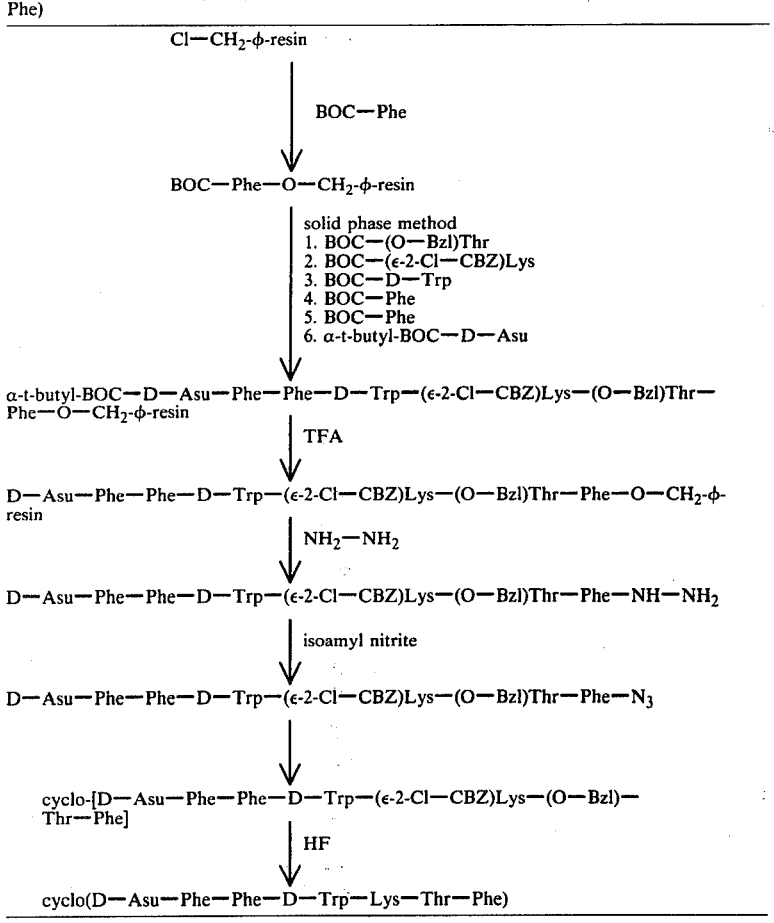

Table III shows another preferred overall procedure for preparing the desired cyclic peptides of the present invention. It involves the stepwise synthesis of a linear peptide on a solid phase resin, and cyclizing the linear peptide to obtain cyclo(D-Asu-Phe-Phe-D-Trp-Lys-Thr-Phe). According to the process, the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids, Thr, Lys, D-Trp, Phe and D-Asu, are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence: D-Asu-Phe-Phe-D-Trp-($\epsilon$-2-Cl-CBZ)-Lys-(O-Bzl)Thr-Phe-NH-NH$_2$ is treated with isoamyl nitrite in acid pH to form the corresponding azide. The azide solution is diluted with solvent and neutralized with an organic base. The linear peptide cyclizes to form cyclo[D-Asu-Phe-Phe-D-Trp-($\epsilon$-2-Cl-CBZ)Lys-(O-Bzl)Thr-Phe]. During the cyclization the "pH" is checked and maintained at neutral by the addition of organic base. The "pH" in organic solvent is determined by the application of an aliquot of the solution to narrow range pH paper.

After the linear peptide is cyclized, the remaining protective groups, 2-Cl-CBZ and Bzl, are removed in one step by treatment with HF in the presence of anisole. The crude cyclic peptides obtained by the processes of Table III are purified by chromatography, preferably on Sephadex eluted with 50% aqueous acetic acid.

The following Examples illustrate methods of carrying out the present invention, but it is to be understood that these Examples are given for purposes of illustration and not of limitation. It is to be understood that by changing the amino acid sequence of the polypeptide in accordance with the instructions provided by this disclosure, affords each of the compounds embraced by the description presented herein and embraced by the claims of this application.

EXAMPLE 1

Preparation of
Cyclo(Aha-Phe-Phe-D-Trp-Lys-Thr-Phe)

Step (a) — Preparation of
D-Trp-($\epsilon$-2-Cl-CBZ)Lys-(O-Bzl)Thr-Phe-Aha-Phe-Phe-O-CH$_2$-$\phi$-Resin Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80°

C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3 × 2000 ml. of tetrahydrofuran
4 × 5170 ml. of ethanol
1 × 5170 ml. of acetic acid
3 × 5170 ml. of water
3 × 5170 ml. of methanol
3 × 5170 ml. of chloroform.

The BOC-Phe-O-CH$_2$-$\phi$-resin was dried in vacuo at 25° C. for 16 hours, giving 1203 g. of BOC-Phe-O-CH$_2$-$\phi$-resin containing 0.937 mmole of phenylalanine/g. of resin.

BOC-Phe-O-CH$_2$-$\phi$-resin (2.84 g.; 2.0 mmole) was carried through the procedures in Tables IV and V using 2 deblockings (2 minutes and 25 minutes) with 25% TFA in methylene chloride, and 2.5 equivalents of BOC-amino acid in the required sequence until the desired BOC-octapeptide-O-CH$_2$-$\phi$-resin was obtained.

DCCI was used as the coupling agent in every step except the coupling of BOC-Phe to Aha-Phe-Phe-O-CH$_2$-$\phi$-resin in which case the coupling was carried out in the presence of DCCI and 1-hydroxybenzotriazole monohydrate (HBT.H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the $\epsilon$-amino group of Lys with 2-Cl-CBZ.

When the desired BOC-heptapeptide-O-CH$_2$-$\phi$-resin was obtained, the N-terminal BOC group was removed by the terminal deblocking procedure set forth in Table VI.

TABLE V

| Protected Amino Acid | Solvent ml. |
|---|---|
| BOC-Phe (1.33 g.) | CH$_2$Cl$_2$, 25 ml. |
| recouple | |
| BOC-Aha (1.23 g.) | CH$_2$Cl$_2$, 25 ml. |
| recouple | |
| BOC-Phe (1.33 g.) + HBT . H$_2$O (1.53 g.) | DMF, 25 ml. |
| recouple | |
| BOC-(O-Bzl)Thr (1.55 g.) | CH$_2$Cl$_2$, 25 ml. |
| recouple | |
| BOC-($\epsilon$-2-Cl-CBZ)Lys (2.08 g.) | CH$_2$Cl$_2$, 25 ml. |
| recouple | |
| BOC-D-Trp (1.52 g.) | DMF, 5.5 ml. |
| | CH$_2$Cl$_2$, 19.5 ml. |
| recouple | |

TABLE VI
TERMINAL DEBLOCKING PROGRAM

| Solvent or reagent (number of treatments or washes | CHCl$_3$ (1) | 25% TFA in CH$_2$Cl$_2$ + 1% Ethanedithiol (2) | CHCl$_3$ (3) | MeOH (2) CH$_2$Cl$_2$ (1) MeOH (2) CH$_2$Cl$_2$ (2) |
|---|---|---|---|---|
| Vol. in ml. | 60 | 60 | 60 | 60 |
| Time in minutes | 5 | 2 and 25 | 2 | 2 |

After the sequence of Tables IV, V and VI were completed, the blocked heptapeptide-O-CH$_2$-$\phi$-resin was filtered, washed with MeOh 3 × 40 ml. (3 minutes per wash) and dried overnight in vacuo. It weighed 3.41 g.

Step (b) — Preparation of
D-Trp-($\epsilon$-2-Cl-CBZ)-Lys-(O-Bzl)Thr-Phe-Aha-Phe-Phe-NH-NH$_2$ To a mixture of 3.20 g. D-Trp-($\epsilon$-2-Cl-CBZ)Lys-(O-Bzl)Thr-Phe-Aha-Phe-Phe-O-CH$_2$-$\phi$-resin in 33 ml. freshly degassed DMF was added 3.3 ml. NH$_2$-NH$_2$. The mixture was magnetically stirred at room temperature for 1 hour. The mixture was filtered to remove the resin. The resin was washed with 4 × 10 ml. DMF. The filtrate and washings were concentrated in vacuo to near dryness. The semi-solid residue was triturated with ether to obtain a solid. The solid was collected by filtration and dried in vacuo for 45 min. to yield 3.14 g. crude product. The solid was slurried with 4 × 20 ml. water to remove all traces of formyl hydrazide and dried in vacuo overnight to give 1.81 g. of product.

Step (c) — Preparation of
D-Trp-($\epsilon$-2-Cl-CBZ-)Lys-(O-Bzl)Thr-Phe-Aha-Phe-Phe-N$_3$

TABLE IV

| Solvent or reagent (number of treatments or washes) | CHCl$_3$ (2) | 25% TFA in CH$_2$Cl$_2$ (2) | CHCl$_3$ (3) | NEt$_3$ CH$_2$Cl$_2$ (1:9) (2) | CHCl$_3$ (3) CH$_2$Cl$_2$ (3) | BOC AA in CH$_2$Cl$_2$, DMF or a mixture of both | 0.5M DCCI in CH$_2$Cl$_2$ | DMF (1) MeOH (1) DMF (1) MeOH (1) CHCl$_3$ (2) |
|---|---|---|---|---|---|---|---|---|
| Volume in ml. | 40 | 40 | 40 | 40 | 40 | 25 ml. | 10 | 40 |
| Time in min. | 5 | 2 and 25 | 2 | 5 and 5 | 2 | 5 | 5 min. coupling 30 min. | 2 |

D-Trp-($\epsilon$-2-Cl-CBZ)Lys-(O-Bzl)Thr-Phe-Aha-Phe-Phe-NH-NH$_2$ (1.75 g., 1.39 mmole), prepared by the process set forth in Step (b), was suspended in 20 ml. freshly degassed DMF. The turbid solution was stirred magnetically at −40° C. under a nitrogen atmosphere. To the suspension was added 1.94 ml., 5.07N HCl in THF (8.34 mmole, 6.0 equivalents). The resulting clear acidic solution, "pH" 1.0 to 1.5, was warmed to −25°

C. and 0.215 ml. isoamyl nitrite (1.39 mmole, 1.0 equivalents) was added and stirring continued for 30 minutes. This solution of D-Trp-(ε-2-Cl-CBZ)Lys-(O-Bzl)-Thr-Phe-Aha-Phe-Phe-N$_3$ was used immediately in step (d).

Step (d) — Preparation of Cyclo[Aha-Phe-Phe-D-Trp-(ε-2-Cl-CBZ)Lys-(O-Bzl)Thr-Phe]

The solution of D-Trp-(ε-2-Cl-CBZ)-Lys-(O-Bzl)Thr-Phe-Aha-Phe-Phe-N$_3$ in DMF, obtained by the process set forth in Step (c), was diluted in 1200 ml. freshly degassed DMF, precooled to −40° C. The solution was maintained under a nitrogen atmosphere and allowed to warm to −20° C. during which time the "pH" was maintained at 7.2 to 7.6 by the addition of 1.62 ml. N,N-diisopropylethylamine. The solution was maintained at −16° C. for 24 hours and then kept at 5° C. for an additional 24 hours. During this period 1.95 ml. of N,N-diisopropylethylamine was added to maintain a "pH" of 7.2 to 7.6.

The solution was concentrated in vacuo to a thick oil, washed twice with ether and once with ethyl acetate and triturated with water to give a solid. The solid was collected by filtration and dried in vacuo overnight to give 1.17 g. of product.

Step (e) — Preparation of Cyclo(Aha-Phe-Phe-D-Trp-Lys-Thr-Phe)

Cyclo[Aha-Phe-Phe-D-Trp-(ε-2-Cl-CBZ)-Lys-(O-Bzl)Thr-Phe], 1.15 g., obtained by the process set forth in Step (d), was dissolved in 2 ml. anisole and 20 ml. hydrogen fluoride at dry ice-acetone bath temperature. The solution was stirred magnetically at ice-bath temperature for 1½ hours. The excess hydrogen fluoride was removed in vacuo at ice-bath temperature. The resulting oily residue was maintained in vacuo for an additional ¾ hour at ice-bath temperature and triturated with ethyl acetate to give a solid. The solid was collected by filtration and dried in vacuo to give 674 mg. of product.

Step (f) — Purification of Cyclo(Aha-Phe-Phe-D-Trp-Lys-Thr-Phe)

The cyclo(Aha-Phe-Phe-D-Trp-Lys-Thr-Phe), 654 mg., obtained by the process set forth in step (e), was dissolved in 12 ml. 50% aqueous acetic acid and charged to a column of Sephadex G-50, (5 cm. × 115 cm., 2260 ml.) packed in 50% aqueous acetic acid. The column was eluted with 50% aqueous acetic acid at the rate of 21 ml./10 min./fraction. The effluent was monitored at 280 nm.

Fractions 83 to 91 were combined, concentrated to dryness in vacuo and the residue lyophilized from 20 ml. 10% aqueous acetic acid to give 369 mg. of substantially pure product. A 20 hour acid hydrolysate showed the following amino acid analysis:

|  | μmole/mg. | normalized to phenylalanine |
| --- | --- | --- |
| Lys | 0.874 | 1.02 |
| Thr | 0.832 | 0.97 |
| Phe | 2.57 | 3.00 |
| Trp | 0.532 | 0.62 |

EXAMPLE 2

Preparation of ω-Methyl-D-α-Aminosuberate.HCl

Methanolic HCl (saturated), 72 ml., is added to a suspension of 22.8 g. of D-α-aminosuberic acid in 450 ml. of methanol. The reaction is stirred at 25° C. for 30 minutes, at which time complete solution occurs. The reaction solution is evaporated to dryness and the residual solid is flushed by evaporation of methanol three times. The product is crystallized from methanol on the addition of ether, filtered and dried in vacuo at 25° C. The crude product (18 g.) is recrystallized from methanol:ether to give 13 g. of substantially pure ω-methyl-D-α-aminosuberate.HCl.

EXAMPLE 3

Preparation of α-t-Butyl-ω-Methyl-D-α-Aminosuberate

ω-Methyl-D-α-aminosuberate.HCl, 13 g., is dissolved in a mixture of 811 ml. of t-butyl acetate and 8.65 ml. of perchloric acid and the solution allowed to stand at 25° C. for four days. The reaction solution is extracted with 0.5N HCl (2 × 600 ml.). The combined aqueous solutions are adjusted to pH 7 with sodium bicarbonate and extracted with ether (3 × 700 ml.). The combined ether extracts are dried over anhydrous sodium sulfate, filtered and evaporated to give 5.5 g. of α-t-butyl-ω-methyl-D-α-aminosuberate as an oil.

EXAMPLE 4

Preparation of α-t-Butyl-ω-Methyl-N-BOC-D-α-Aminosuberate

α-t-Butyl-ω-methyl-D-α-aminosuberate, 5.5 g., is dissolved in 80 ml. of DMF. t-Butyl-trichlorophenyl carbonate, 6.0 g., is added and the pH adjusted to 8.5 with triethylamine. Additional triethylamine is added over a period of one hour to maintain a pH of 8.5 and the reaction mixture is stirred overnight at 25° C. The reaction mixture is evaporated to a heavy oil in vacuo and dissolved in 600 ml. of ether. The ether solution is extracted three times with 600 ml. portions of saturated sodium bicarbonate solution, three times with 600 ml. portions of 0.1N H$_2$SO$_4$, and finally, once with 600 ml. of saturated sodium chloride solution. The ether solution is evaporated to dryness to give α-t-butyl-ω-methyl-N-BOC-D-α-aminosuberate, 8.6 g., as a heavy oil.

EXAMPLE 5

Preparation of α-t-Butyl-N-BOC-D-α-Aminosuberate

α-t-Butyl-ω-methyl-N-BOC-D-α-aminosuberate, 5 g., is dissolved in a mixture of 208 ml. of dioxane and 133 ml. of 1.0N sodium hydroxide. The reaction is stirred 1¼ hours at 25° C. and the organic solvent is removed by evaporation in vacuo. After the addition of 150 ml. of water, the solution is brought to a pH of 4.6 by the addition of dilute sulfuric acid and extracted with ether (3 × 150 ml.). The combined ether extracts are dried over anhydrous sodium sulfate and evaporated in vacuo to a heavy syrup. The crude product, 4.5 g., is dissolved in a minimum volume of methylene chloride and applied on a column packed with 400 g. Silica Gel-60 and the by-products eluted with methylene chloride. When no further by-products are detected in the eluate by means of thin layer chromatography, the eluate is changed to a mixture of methylene chloride:isopropanol (98:2) to elute the product. Those fractions which contain product, as determined by thin layer chromatography, are combined and evaporated to dryness in vacuo. Crystallization from hexane gives 1.5 g. of α-t-butyl-N-BOC-D-α-aminosuberate, m.p. 72° to 3° C.

EXAMPLE 6

Preparation of Cyclo(D-Asu-Phe-Phe-D-Trp-Lys-Thr-Phe)

Step (a) — Preparation of D-Asu-Phe-Phe-D-Trp-(ε-2-Cl-CBZ)Lys-(O-Bzl)Thr-Phe-O-CH$_2$-φ-Resin BOC-Phe-O-CH$_2$-φ-resin (2.84 g.; 2.0 mmole) prepared by the process set forth in Example 1 is carried through the procedures in Tables IV and VII using 2 deblockings (2 minutes and 25 minutes) with 25% TFA in methylene chloride, and 2.5 equivalents of BOC-amino acid in the required sequence until the desired BOC-octapeptide-O-CH$_2$-φ-resin is obtained.

The coupling of each amino acid proceeds smoothly. Best yields are obtained when the coupling is repeated in each step. When the coupling is repeated, the initial two chloroform washes, the deblocking step and the succeeding three chloroform washes are all omitted and replaced by a single chloroform wash.

The coupling reaction is carried out in methylene chloride, freshly degassed DMF or a mixture of these two solvents. The N-terminal amino group is blocked with a BOC group in each case; the hydroxy group of Thr is blocked with Bzl and the ε-amino group of Lys with 2-Cl-CBZ.

When the desired BOC-heptapeptide-O-CH$_2$-φ-resin is obtained, the N-terminal BOC group is removed by the terminal deblocking procedure set forth in Table VI.

TABLE VII

| Protected Amino Acid | Solvent ml. |
| --- | --- |
| BOC-(O-Bzl)Thr (1.55 g.) | CH$_2$Cl$_2$, 25 ml. |
| recouple | CH$_2$Cl$_2$, 25 ml. |
| BOC-(ε-2-Cl-CBZ)Lys (2.08 g.) | |
| recouple | |
| BOC-D-Trp (1.52 g.) | DMF, 5.5 ml. |
| recouple | CH$_2$Cl$_2$, 19.5 ml. |
| BOC-Phe (1.33 g.) | CH$_2$Cl$_2$, 25 ml. |
| recouple | |
| BOC-Phe (1.33 g.) | DMF, 25 ml. |
| recouple | |
| α-t-butyl-BOC-D-α-Asu (0.864 g.) | CH$_2$Cl$_2$, 25 ml. |
| recouple | |

After the sequence of Tables IV, VII and VI is completed, the blocked heptapeptide-O-CH$_2$-φ-resin is filtered, washed with MeOH 3 × 40 ml. (3 minutes per wash) and dried overnight in vacuo.

Step (b) — Preparation of D-Asu-Phe-Phe-D-Trp-(ε-2-Cl-CBZ)Lys-(O-Bzl)Thr-Phe-NH-NH$_2$ To a mixture of D-Asu-Phe-Phe-D-Trp-(ε-2-Cl-CBZ)Lys-(O-Bzl)Thr-Phe-O-CH$_2$-φ-resin obtained in Example 6, Step (a) in 33 ml. freshly degassed DMF is added 3.3 ml. NH$_2$—NH$_2$. The mixture is magnetically stirred at room temperature for 1 hour. The mixture is filtered to remove the resin. The resin is washed with 4 × 10 ml. DMF. The filtrate and washings are concentrated in vacuo to near dryness. The semi-solid residue is triturated with ether to obtain a solid. The solid is collected by filtration and dried in vacuo for 45 min. to yield crude product. The solid is slurried with 4 × 20 ml. water to remove all traces of formyl hydrazide and dried in vacuo overnight to give the desired product.

Step (c) — Preparation of D-Asu-Phe-Phe-D-Trp-(ε-2-Cl-CBZ)Lys-(O-Bzl)Thr-Phe-N$_3$ D-Asu-Phe-Phe-D-Trp-(ε-2-Cl-CBZ)Lys-(O-Bzl)-Thr-Phe-NH-NH$_2$, prepared by the process set forth in Example 6, Step (b), is suspended in 20 ml. freshly degassed DMF. The turbid solution is stirred magnetically at −40° C. under a nitrogen atmosphere. To the suspension is added 1.94 ml., 5.07N HCl in THF (8.34 mmole). The resulting clear acidic solution, "pH" 1.0 to 1.5 is warmed to −25° C. and isoamyl nitrite (1.0 equivalent) is added and stirring continued for 30 minutes. This solution of D-Asu-Phe-Phe-D-Trp-(ε-2-Cl-CBZ)Lys-(O-Bzl)Thr-Phe-N$_3$ is used immediately in Step (d).

Step (d) — Preparation of Cyclo[D-Asu-Phe-Phe-D-Trp-(ε-2-Cl-CBZ)Lys-(O-BZl)Thr-Phe]

The solution of D-Asu-Phe-Phe-D-Trp-(ε-2-Cl-CBZ)Lys-(O-Bzl)Thr-Phe-N$_3$ in DMF, obtained by the process set forth in Example 6, Step (c), is diluted in 1200 ml. freshly degassed DMF, precooled to −40° C. The solution is maintained under a nitrogen atmosphere and allowed to warm to −20° C. during which time the "pH" was maintained at 7.2 to 7.6 by the addition of N,N-diisopropylethylamine. The solution is maintained at −16° C. for 24 hours and then kept at 5° C. for an additional 24 hours. During this period N,N-diisopropylethylamine is added to maintain a "pH" of 7.2 to 7.6.

The solution is concentrated in vacuo to a thick oil, washed twice with ether and once with ethyl acetate and triturated with water to give a solid. The solid was collected by filtration and dried in vacuo overnight to give the desired product.

Step (e) — Preparation of Cyclo(D-Asu-Phe-Phe-D-Trp-Lys-Thr-Phe)

Cyclo[D-Asu-Phe-Phe-D-Trp-(ε-2-Cl-CBZ)Lys-(O-BZl)Thr-Phe], obtained by the process set forth in Example 6, Step (d), is dissolved in 2 ml. anisole and 20 ml. hydrogen fluoride at dry ice-acetone bath temperature. The solution is stirred magnetically at ice-bath temperature for 1½ hours. The excess hydrogen fluoride is removed in vacuo at ice-bath temperature. The resulting oily residue is maintained in vacuo for an additional ¾ hour at icebath temperature and triturated with ethyl acetate to give a solid. The solid is collected by filtration and dried in vacuo to give the desired product.

Step (f) — Purification of Cyclo(D-Asu-Phe-Phe-D-Trp-Lys-Thr-Phe)

The cyclo(D-Asu-Phe-Phe-D-Trp-Lys-Thr-Phe), obtained by the process set forth in Example 6, Step (e), is dissolved in 12 ml. 50% aqueous acetic acid and charged to a column of Sephadex G-50, (5 cm. × 115 cm., 2260 ml.) packed in 50% aqueous acetic acid. The column is eluted with 50% aqueous acetic acid at the rate of 21 ml./10 min./fraction. The effluent is monitored at 280 nm.

Fractions containing the product are combined, concentrated to dryness in vacuo and the residue lyophilized from 20 ml. 10% aqueous acetic acid to give substantially pure product.

The somatostatin analogs of the present invention and the non-toxic pharmaceutically acceptable salts thereof, are useful in humans and animals for inhibiting growth hormone release as in the treatment of acromegaly, inhibiting the release of glucagon and alone or in conjunction with insulin, for lowering blood glucose as in the treatment of diabetes with reduced gastrointestinal side effects. In the treatment of diabetes, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg. to about 7 mg./kg. of body weight per day. These somatostatin analogs are preferably administered by injection. A therapeutically effective amount of an analog is ordinarily supplied at a dosage level of from about 0.001 mg. to about 2 mg./kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of cyclo(Aha-Phe-Phe-D-Trp-Lys-Thr-Phe) suitable for subcutaneous injection.

EXAMPLE 7

1 ml. sterile saline;

1 mg. cyclo(Aha-Phe-Phe-D-Trp-Lys-Thr-Phe).

What is claimed is:

1. Compounds of the formula:

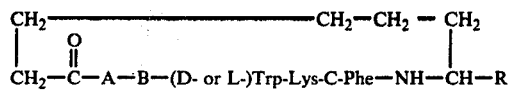

wherein
A is Phe, Tyr, O-Me-Tyr,
B is Phe, Tyr,
C is Thr, Val,
R is H, COOH,
wherein the ring formed by the peptide backbone contains 26 atoms and pharmaceutically acceptable non-toxic acid addition salts and carboxylic acid salts thereof.

2. The compound according to claim 1 having the formula:

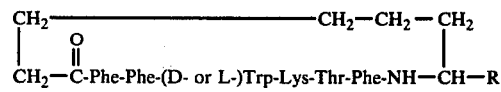

wherein R is H, COOH.

3. A composition comprising a therapeutically effective amount of the peptides having the structure:

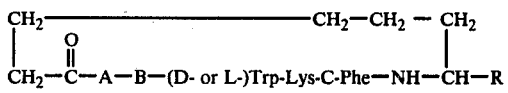

wherein
A is Phe, Tyr, O-Me-Tyr,
B is Phe-Tyr,
C is Thr, Val,
R is H, COOH,
wherein the ring formed by the peptide backbone contains 26 atoms and pharmaceutically acceptable non-toxic acid addition salts and carboxylic acid salts thereof in a pharmaceutically acceptable excipient.

* * * * *